(12) United States Patent
Gyrn

(10) Patent No.: US 9,440,051 B2
(45) Date of Patent: Sep. 13, 2016

(54) INSERTER FOR A MULTIPLICITY OF SUBCUTANEOUS PARTS

(71) Applicant: Unomedical A/S, Birkerød (DK)

(72) Inventor: Steffen Gyrn, Ringsted (DK)

(73) Assignee: UNOMEDICAL A/S, Birkeroed (DK)

( * ) Notice: Subject to any disclaimer, the term of this patent is extended or adjusted under 35 U.S.C. 154(b) by 0 days.

(21) Appl. No.: 13/658,125

(22) Filed: Oct. 23, 2012

(65) Prior Publication Data

US 2013/0110047 A1 May 2, 2013

Related U.S. Application Data

(60) Provisional application No. 61/552,085, filed on Oct. 27, 2011.

(30) Foreign Application Priority Data

Oct. 27, 2011 (EP) .................................... 11186868

(51) Int. Cl.
*A61M 25/06* (2006.01)
*A61M 5/00* (2006.01)
(Continued)

(52) U.S. Cl.
CPC .......... *A61M 25/0612* (2013.01); *A61B 5/1411* (2013.01); *A61B 5/150022* (2013.01);
(Continued)

(58) Field of Classification Search
CPC .......... A61B 5/15151; A61B 17/3468; A61B 5/150435; A61B 5/15176; A61B 5/15144; A61M 2005/004; A61M 2005/005; A61M 25/0606; A61M 2005/1587; A61M 2005/3022; A61M 25/0612

USPC .................... 604/136, 173, 174, 164.01
See application file for complete search history.

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4 342 329 A1 | 6/1994 |
| DE | 196 31 921 A1 | 3/1997 |

(Continued)

OTHER PUBLICATIONS

"Why inset®?" inset® infusion set product overview; http://web.archive.org/web/20040906102448/http://www.infusion-set.com/Default.asp?ID=108; two pages.

*Primary Examiner* — Theodore Stigell
*Assistant Examiner* — Benjamin Koo
(74) *Attorney, Agent, or Firm* — Wilson Sonsini Goodrich & Rosati

(57) ABSTRACT

A holding device and an inserter are provided. The holding device includes a casing providing a cavity including walls, the was encompass a subcutaneous unit. The cavity includes a first side having an outlet opening, the outlet opening before use is covered with a penetrable or removable cover, and a second side comprising a layer having an outer surface and being penetrable, removable or flexible to transfer an impact from outside the layer to the subcutaneous unit. The casing includes a releasable attachment member corresponding to a member on the subcutaneous unit and a needle secured to the casing. An impact towards the outer surface of the layer pushes the subcutaneous unit at least partly out of the casing into a subcutaneous position, when the unit is in the subcutaneous position the releasable attachment member of the casing is released allowing detachment of the unit from the casing.

7 Claims, 8 Drawing Sheets

(51) Int. Cl.
  *A61B 5/15* (2006.01)
  *A61B 5/151* (2006.01)
  *A61M 5/158* (2006.01)

(52) U.S. Cl.
  CPC ....... *A61B 5/15105* (2013.01); *A61B 5/15113* (2013.01); *A61B 5/15117* (2013.01); *A61B 5/15144* (2013.01); *A61B 5/15151* (2013.01); *A61B 5/15163* (2013.01); *A61B 5/15176* (2013.01); *A61B 5/150435* (2013.01); *A61B 5/150519* (2013.01); *A61B 5/150564* (2013.01); *A61B 5/150717* (2013.01); *A61M 5/158* (2013.01); *A61M 25/0631* (2013.01); *A61M 2005/004* (2013.01)

(56) References Cited

U.S. PATENT DOCUMENTS

| | | | |
|---|---|---|---|
| 2,295,849 | A | 9/1942 | Kayden |
| 2,690,529 | A | 9/1954 | Lindblad |
| 2,972,779 | A | 2/1961 | Cowley |
| 3,059,802 | A | 10/1962 | Mitchell |
| 3,074,541 | A | 1/1963 | Roehr |
| 3,149,186 | A | 9/1964 | Coanda |
| 3,221,739 | A | 12/1965 | Rosenthal |
| 3,221,740 | A | 12/1965 | Rosenthal |
| 3,306,291 | A | 2/1967 | Burke |
| 3,485,352 | A | 12/1969 | Pilger |
| 3,509,879 | A | 5/1970 | Bathish et al. |
| 3,519,158 | A | 7/1970 | Anderson |
| 3,547,119 | A | 12/1970 | Hall et al. |
| 3,575,337 | A | 4/1971 | Bernhardt |
| 3,610,240 | A | 10/1971 | Harautuneian |
| 3,615,039 | A | 10/1971 | Ward |
| 3,670,727 | A | 6/1972 | Reiterman |
| 3,783,895 | A | 1/1974 | Weichselbaum |
| 3,788,374 | A | 1/1974 | Saijo |
| 3,810,469 | A | 5/1974 | Hurschman |
| 3,835,862 | A | 9/1974 | Villari |
| 3,840,011 | A | 10/1974 | Wright |
| 3,893,448 | A | 7/1975 | Brantigan |
| 3,937,219 | A | 2/1976 | Karakashian |
| 3,986,507 | A | 10/1976 | Watt |
| 3,986,508 | A | 10/1976 | Barrington |
| 3,995,518 | A | 12/1976 | Spiroff |
| 4,022,205 | A | 5/1977 | Tenczar |
| 4,188,950 | A | 2/1980 | Wardlaw |
| 4,201,406 | A | 5/1980 | Dennehey et al. |
| 4,227,528 | A | 10/1980 | Wardlaw |
| 4,259,276 | A | 3/1981 | Rawlings |
| 4,267,836 | A | 5/1981 | Whitney et al. |
| 4,296,786 | A | 10/1981 | Brignola |
| 4,315,505 | A | 2/1982 | Crandall et al. |
| 4,333,455 | A | 6/1982 | Bodicky |
| 4,334,551 | A | 6/1982 | Pfister |
| D267,199 | S | 12/1982 | Koenig |
| 4,378,015 | A | 3/1983 | Wardlaw |
| 4,402,407 | A | 9/1983 | Maly |
| 4,415,393 | A | 11/1983 | Grimes |
| 4,417,886 | A | 11/1983 | Frankhouser et al. |
| 4,464,178 | A | 8/1984 | Dalton |
| 4,473,369 | A | 9/1984 | Lueders et al. |
| 4,484,910 | A | 11/1984 | Sarnoff et al. |
| 4,500,312 | A | 2/1985 | McFarlane |
| 4,508,367 | A | 4/1985 | Oreopoulos et al. |
| 4,525,157 | A | 6/1985 | Vaillancourt |
| 4,530,695 | A | 7/1985 | Phillips et al. |
| 4,531,937 | A | 7/1985 | Yates |
| 4,543,088 | A | 9/1985 | Bootman et al. |
| 4,563,177 | A | 1/1986 | Kamen |
| 4,610,469 | A | 9/1986 | Wolff-Mooij |
| 4,617,019 | A | 10/1986 | Fecht |
| 4,713,059 | A | 12/1987 | Bickelhaupt et al. |
| 4,734,092 | A | 3/1988 | Millerd |
| 4,755,173 | A | 7/1988 | Konopka et al. |
| 4,817,603 | A | 4/1989 | Turner et al. |
| RE32,922 | E | 5/1989 | Levin et al. |
| 4,838,871 | A | 6/1989 | Luther |
| 4,840,613 | A | 6/1989 | Balbierz |
| 4,850,974 | A | 7/1989 | Bickelhaupt et al. |
| 4,850,996 | A | 7/1989 | Cree |
| 4,863,016 | A | 9/1989 | Fong et al. |
| 4,878,897 | A | 11/1989 | Katzin |
| 4,890,608 | A | 1/1990 | Steer |
| 4,894,054 | A | 1/1990 | Miskinyar |
| 4,895,570 | A | 1/1990 | Larkin |
| 4,917,669 | A | 4/1990 | Bonaldo |
| 4,935,010 | A | 6/1990 | Cox et al. |
| 4,950,163 | A | 8/1990 | Zimble |
| 4,950,252 | A | 8/1990 | Luther et al. |
| 4,956,989 | A | 9/1990 | Nakajima |
| 4,969,870 | A * | 11/1990 | Kramer ................ A61B 10/025 604/264 |
| 4,970,954 | A | 11/1990 | Weir et al. |
| 4,978,338 | A | 12/1990 | Melsky et al. |
| 4,982,842 | A | 1/1991 | Hollister |
| 4,986,817 | A | 1/1991 | Code |
| 4,994,042 | A | 2/1991 | Vadher |
| 4,994,045 | A | 2/1991 | Ranford |
| 5,011,475 | A | 4/1991 | Olsen |
| 5,020,665 | A | 6/1991 | Bruno |
| 5,024,662 | A | 6/1991 | Menes et al. |
| 5,067,496 | A | 11/1991 | Eisele |
| 5,092,853 | A | 3/1992 | Couvertier, II |
| 5,098,389 | A | 3/1992 | Cappucci |
| 5,112,313 | A | 5/1992 | Sallee |
| 5,116,319 | A | 5/1992 | Van den Haak |
| 5,116,325 | A | 5/1992 | Paterson |
| 5,121,751 | A | 6/1992 | Panalletta |
| 5,129,884 | A | 7/1992 | Dysarz |
| 5,135,502 | A | 8/1992 | Koenig, Jr. et al. |
| 5,137,516 | A | 8/1992 | Rand et al. |
| 5,137,524 | A | 8/1992 | Lynn et al. |
| 5,141,496 | A | 8/1992 | Dalto et al. |
| 5,147,375 | A | 9/1992 | Sullivan et al. |
| 5,163,915 | A | 11/1992 | Holleron |
| 5,172,808 | A | 12/1992 | Bruno |
| 5,176,643 | A | 1/1993 | Kramer et al. |
| 5,176,650 | A | 1/1993 | Haining |
| 5,176,662 | A | 1/1993 | Bartholomew et al. |
| 5,186,712 | A | 2/1993 | Kelso et al. |
| 5,188,611 | A | 2/1993 | Orgain |
| RE34,223 | E | 4/1993 | Bonaldo |
| 5,205,820 | A | 4/1993 | Kriesel |
| 5,222,947 | A | 6/1993 | D'Amico |
| 5,232,454 | A | 8/1993 | Hollister |
| 5,248,301 | A | 9/1993 | Koenig et al. |
| 5,256,149 | A | 10/1993 | Banik et al. |
| 5,256,152 | A | 10/1993 | Marks |
| 5,257,980 | A | 11/1993 | Van Antwerp et al. |
| 5,267,963 | A | 12/1993 | Bachynsky |
| 5,269,799 | A | 12/1993 | Daniel |
| 5,271,744 | A | 12/1993 | Kramer et al. |
| 5,279,579 | A | 1/1994 | D'Amico |
| 5,279,591 | A | 1/1994 | Simon |
| 5,282,793 | A | 2/1994 | Larson |
| 5,300,030 | A | 4/1994 | Crossman et al. |
| 5,312,359 | A | 5/1994 | Wallace |
| 5,312,369 | A | 5/1994 | Arcusin et al. |
| 5,316,246 | A | 5/1994 | Scott et al. |
| 5,324,302 | A | 6/1994 | Crouse |
| 5,342,319 | A | 8/1994 | Watson et al. |
| 5,342,324 | A | 8/1994 | Tucker |
| 5,344,007 | A | 9/1994 | Nakamura et al. |
| 5,350,392 | A | 9/1994 | Purcell et al. |
| 5,354,280 | A | 10/1994 | Haber et al. |
| 5,354,337 | A | 10/1994 | Hoy |
| 5,366,469 | A | 11/1994 | Steg et al. |
| 5,372,592 | A | 12/1994 | Gambale |
| 5,372,787 | A | 12/1994 | Ritter |
| 5,376,082 | A | 12/1994 | Phelps |
| 5,379,895 | A | 1/1995 | Foslien |
| 5,384,174 | A | 1/1995 | Ward et al. |
| 5,387,197 | A | 2/1995 | Smith et al. |

(56) References Cited

U.S. PATENT DOCUMENTS

| | | |
|---|---|---|
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,568,806 A * | 10/1996 | Cheney et al. ............... 600/373 |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |

(56) References Cited

U.S. PATENT DOCUMENTS

| | | |
|---|---|---|
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Scheider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0212362 A1* | 11/2003 | Roser .................... 604/110 |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |

(56) References Cited

U.S. PATENT DOCUMENTS

| | | |
|---|---|---|
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1* | 8/2004 | Bengtsson ................ 604/136 |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015066 A1* | 1/2006 | Turieo et al. ................ 604/136 |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |
| 2013/0338597 A1* | 12/2013 | McAllister ................ 604/173 |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |

(56) References Cited

FOREIGN PATENT DOCUMENTS

| | | |
|---|---|---|
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 6/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/20021 A1 | 7/1996 |
| WO | WO 96/32981 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |

(56) References Cited

FOREIGN PATENT DOCUMENTS

| | | |
|---|---|---|
| WO | WO 2008/092959 A1 | 8/2008 |
| WO | WO 2008/133702 A1 | 11/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |

\* cited by examiner

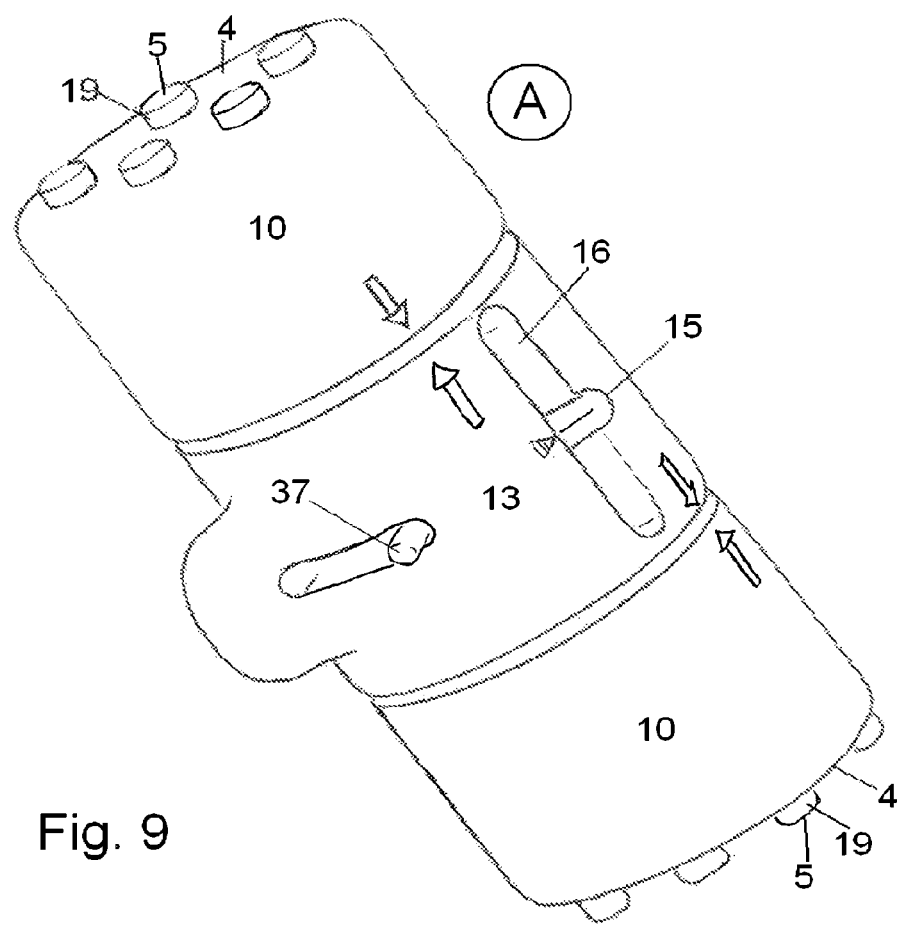
Fig. 9
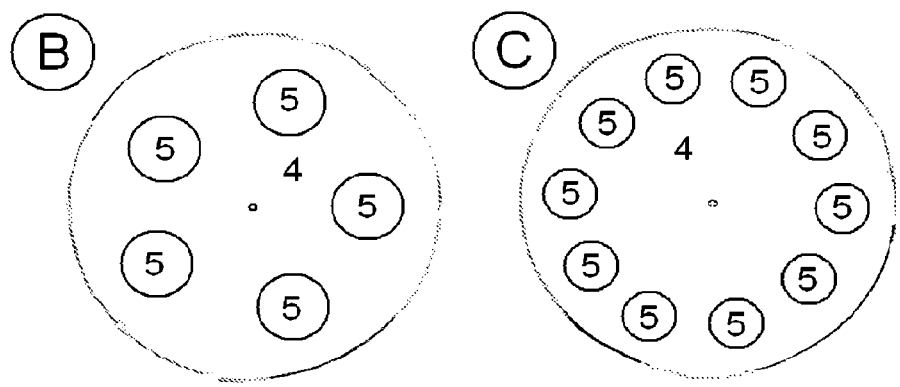

INSERTER FOR A MULTIPLICITY OF SUBCUTANEOUS PARTS

RELATED APPLICATIONS

This application claims the benefit of U.S. Provisional Application No. 61/552,085, filed Oct. 27, 2011, and European Application 11186868.3, filed Oct. 27, 2011, which are incorporated by reference herein in their entirety.

TECHNICAL FIELD OF THE INVENTION

The invention relates to a cartridge i.e. a holding device containing parts to be placed subcutaneously and an inserter for a cartridge i.e. a holding device containing parts to be placed subcutaneously.

Each cartridge provides sterile storing and feeding of a multiplicity of subcutaneous parts such as cannula parts or sensors or the like to an inserter. The cartridge is either integral with the inserter i.e. secured unreleasably to the inserter or replaceable i.e. detachable from the inserter. The cartridge functions by holding and positioning the subcutaneous parts relative to the inserter.

The inserter can be used for inserting one or more subcutaneous parts into a different infusion sites positioned on a patients skin before use.

BACKGROUND OF THE INVENTION

The document WO 2004/030726 discloses a needle device comprising a housing, a base portion having a mounting surface adapted for application to the skin of a patient and a plurality of needles. Each needle comprises a distal pointed end adapted to penetrate the skin of a patient and each needle has a first position in which the distal end is retracted relative to the mounting surface and a second position in which the distal end projects from the mounting surface. A needle device according to this document being mounted on the patients has to have a height at least corresponding to the length of a needle as the needles before and after use are retracted in their full length perpendicular to the mounting surface, also the cannulas according to the shown embodiments have to be hard, self-penetrating cannulas provided with a side net opening. According to WO 2004/030726 the inserter parts are an integrated part of the device, it is not possible to separate the inserter from the parts to be inserted.

The document US2004/158207, FIGS. 13-18, discloses an inserter for insertion of a cannula part where the inserter is provided with an insertion needle. When the cannula part is attached to the inserter, the sterility of the subcutaneous part of the cannula part is compromised. Thus, insertion has to take place shortly after the cannula part has been exposed to the surroundings in order to avoid contamination of the cannula part.

The document WO 99/33504 discloses an inserter for insertion of an infusion part wherein the inserter is provided with a plunger and no insertion needle. The insertion needle is part of the infusion set and is removed from the infusion set after the set has been inserted and the inserter has been removed. As soon as the infusion set is placed in the inserter, the sterility of the subcutaneous part of the infusion set is compromised. Thus, insertion has to take place shortly after the cannula part has been exposed to the surroundings in order to avoid contamination of the cannula part.

SUMMARY OF THE INVENTION

According to the present invention, the sterility of the technical part to be subcutaneously inserted is maintained although the holding part is attached to the inserter. By applying a dosed cartridge instead of an unprotected infusion set solves the problem of preparing the device for insertion while maintaining the sterility of the subcutaneous part. Also applying a cartridge makes it possible to apply a holding device holding a multiplicity of technical parts.

The object of the invention is to provide a holding device holding one or more technical parts under sterile conditions, the device comprising:
- a technical part (1, 2) for subcutaneous positioning comprising a body part (1) which after detachment from the holding device is positioned above the patients skin surface and a longish part (2) which after detachment from the holding device is positioned at least partly below the patients skin surface,
- a casing providing at least one cavity (3) comprising was where the walls encompasses one technical part (1, 2), said cavity (3) having a first side (4) comprising an outlet opening (5) which before use is covered with a penetrable or removable cover (11), and a second side (6) comprising a layer having an outer surface and being either penetrable (18) or removable or flexible (7) in order to transfer an impact from outside the layer to the technical part (1, 2),
- a sharp needle (9) either being part of the technical part (1, 2) or of the casing, wherein an impact towards the outer surface of the layer (7, 18) of the second side (6) pushes the technical part (1, 2) at least partly out of the casing.

The walls encompassing the technical parts are solid meaning that they cannot be penetrated by fingers or sharp needles.

The first and second sides need not be positioned opposite each other, although this is the case for the shown embodiments.

The layer of the second side can be either penetrable i.e. be constituted of a layer of paper or similar brittle material, or the layer can be either a manually or an automatically removable layer i.e. the layer will be removed just before the act of inserting technical part either manually as the user peels of the layer of the specific cavity or automatically as e.g. turning of the holding device relative to the inserter will remove the layer from the second side of the specific cavity.

According to one embodiment the casing comprises at least two cavities, where each cavity (3) encompasses one technical part (1, 2).

According to one embodiment the holding device comprises attachment means (17) attaching the holding device to and interacting with an inserter able to provide an impact toward the outer surface of the layer (7, 18) of the second side (6) of the casing.

According to one embodiment the sharp needle (9) is part of the casing. This means that the sharp needle is an integrated part of the casing and it cannot be removed from the casing without using violence. The casing of this embodiment can comprise, a spring unit (7) providing retraction of the sharp needle (9) after insertion of the technical part (1, 2). Such a spring unit (7) can either comprise
- an elastic unit attached close to or at the second side (6) and to the distal end of the sharp needle (9) which elastic unit pulls the sharp needle (9) into a retracted position when biased or
- an elastic unit positioned between the distal end of the sharp needle (9) or of a proximal surface of a needle hub (8) to which the sharp needle (9) is attached and the first side (4) which elastic unit pushes the sharp needle (9) into a retracted position after detachment of the technical part (1, 2).

According to one embodiment the technical part comprises attachment means attaching the technical part to an infusion site at a point during insertion of the technical part. The attachment means can be positioned on the proximal side of the technical device (1, 2) here defined as the side of the technical device where from the longish part (2) extends.

According to one embodiment the casing comprises guiding parts (19) corresponding to receiving or guiding parts (33) of an infusion site, where joining of the corresponding guiding parts ensure correct positioning of the casing relative to the infusion site.

According to another aspect, the invention also relates to a combination comprising a holding device according to the previous description an inserter comprising a plunger (22) which plunger upon activation penetrates or pushes away the layer of the second side (6) and provides an impact to the technical part (1, 2). The inserter can comprise a lancet (36) and an actuator (37) for this lancet which lancet upon actuation will be inserted between 0.5-5.5 mm below a skin surface when pressed against the skin surface.

DEFINITIONS

"Distal" as used herein refers to a surface or part furthest or further away from the patient's skin surface than other surfaces or parts in question.

"Proximal:" as used herein refers to a surface or part closest to or closer to the patient's skin surface then other surfaces or parts in question.

"Insertion site" refers in the application text to a part which is attached to a patient's skin surface prior to insertion of a technical part and into or through which a technical part is or can be inserted.

BRIEF DESCRIPTION OF THE DRAWINGS

A detailed description of embodiments of the current invention will be made with reference to the accompanying figures, wherein like numerals designate corresponding parts in different figures.

FIG. 1A shows the holding device in a ready-to-use state and FIG. 1B shows the holding device in a use-state just before the technical part is fully inserted.

FIG. 4A shows a partly cut-through view of the inside of the multiple cavity holding, FIG. 4B shows a bottom view of the multiple cavity holding, FIG. 4C shows a top view of the multiple cavity holding and FIG. 4D shows an enlargement of the open end of a cavity provided with a sterility cover.

FIG. 7B shows details on the attachment means of the inserter and of the multiple cavity holding device.

FIGS. 9A-C show an embodiment of an inserter and holding devices to be used with this embodiment of the inserter.

DETAILED DESCRIPTION OF THE INVENTION

Figure 1:
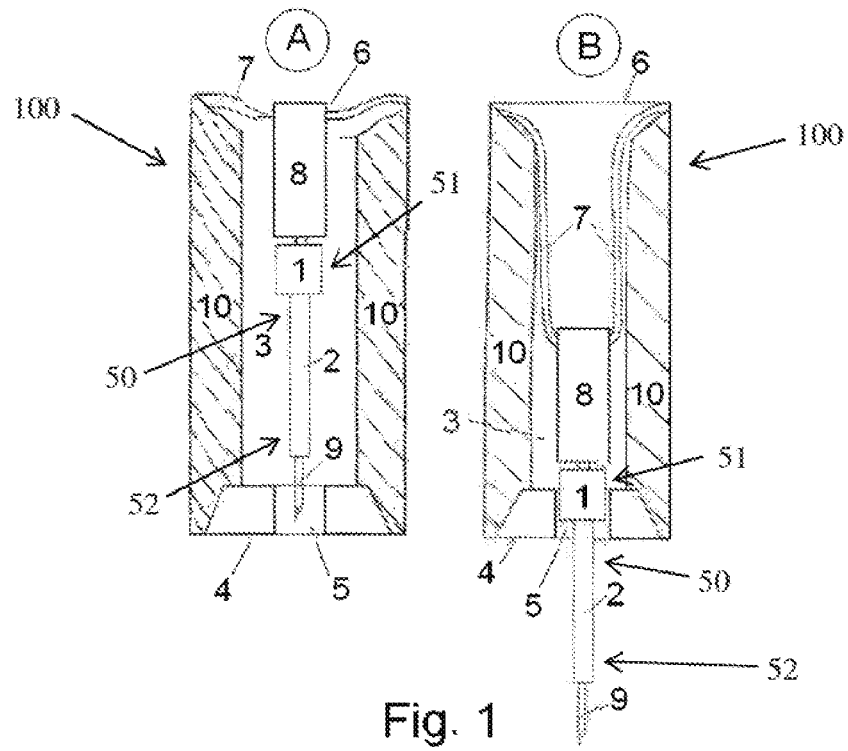
FIGS. 1A-B show an embodiment of a holding device according to the invention.

FIG. 1 shows an embodiment of a holding device 100 according to the invention. The holding device holds a technical part 50 which according to this embodiment is a cannula part. The cannula part comprises a body part 1 which stays above the patient's skin surface after insertion and a longish part 2 which is at least partly inserted into a cavity cut in the patient's skin. The longish part 2 of the shown embodiment is a soft cannula i.e. a hollow tube which is not able to penetrate the patient's skin on its own. The technical part has a proximal side 51 and a distal side 52.

The holding device is provided with a protected cavity 3 in which sterile conditions can be upheld until use. The cavity is encompassed by a casing having a first side 4 comprising an outlet 5 and a second side 6 at least partly covered with a flexible layer or spring unit 7. A needle hub 8 is attached unreleasably i.e. is secured to the flexible layer 7 and a sharp needle i.e. insertion needle 9 extends from the proximal end of the needle hub 8.

According to alternative embodiments of the invention, the technical part might itself comprise a penetrating longish part 2. According to other alternative embodiments of the invention, the sharp needle 9 could be inserted together with the technical part and then removed after the casing has been removed from the insertion site. Both alternatives would make it unnecessary to provide the casing with a sharp needle.

The casing of FIG. 1 is provided with sides or walls 10 extending in the direction of insertion. These longitudinally extending sides 10 together provide a tube-like structure for the cavity 3 in which the needle hub 8 together with the insertion needle 9 and the technical part 1, 2 can move back and forth. The cavity 3 and/or the outer surface of the casing might show a round or oval or cylindrical cross-sectional area. If the outer surface of the casing shows a round cross-sectional area, then the holding device is cylindrical.

According to alternative embodiments showing a similar function, the second side 6 could consist of a brittle cover such as gas-penetrable paper which can be broken when subjected to an impact but which will also uphold a sterility border towards the surroundings. According to such an alternative embodiment, a spring unit 7, such as a metal helical spring, could be placed between the needle hub 8 and the first side 4.

FIG. 1A shows the holding device in a ready-to-use state where a sterility cover has been removed from the first side 4 such that the outlet 5 is open. The sterility cover covering the outlet 5 before use prevents access of microorganism during storage. In this state the spring unit 7 is un-biased and the technical part 1, 2 together with the needle hub 8 and the attached sharp needle 9 is in a retracted position.

FIG. 1B shows the holding device in a use-state just before the technical part is fully inserted. In this state the spring unit 7 is almost fully biased and the technical part 1, 2 together with the needle hub 8 and the attached sharp needle 9 is in a forward position.

Figure 2:
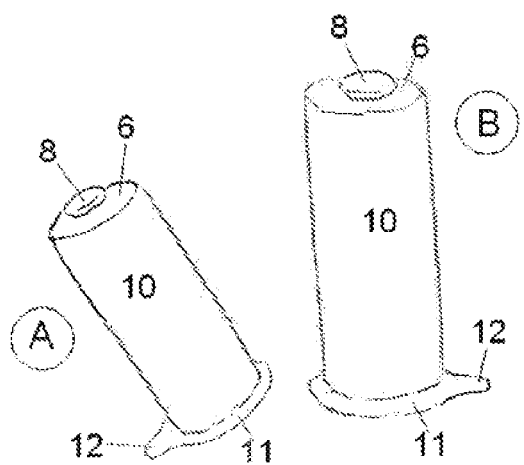
FIG. 2 shows two embodiments of single cavity holding devices.

FIG. 2 shows two embodiments of holding devices according to the inventions. FIG. 2A shows a cylindrical casing containing a cannula part which is very small. The size of the cannula part is reflected in the size of the casing, which is also relatively small. FIG. 2B shows a cylindrical casing containing a sensor part which is larger than the casing holding the cannula part. Generally, there might exist sensor parts being smaller or same size as a cannula part. Both casings are provided with a sterility cover 11 attached to the first side 4 and fully covering the outlet 5. According to these embodiments, the sterility cover 11 is a paper, plastic or textile welded to the first side 4 of the casing in such a way that the cover 11 can be removed by pulling a snip 12 at the edge of the cover 11.

When a technical part 1, 2 is to be inserted subcutaneously, the user, which night be the patient but which could also be another person, first removes the cover 11 by pulling the snip 12. Secondly, the proximal end of the casing is positioned at the insertion site. Normally the proximal end of the casing is provided with guiding means which makes the proximal end of the casing fit into the insertion site and make it easy for the user to position the casing correctly. Third, the user presses towards the distal end i.e. the second end of the casing. This can be done manually either with a finger or with a tool such as e.g. a pencil. Alternatively, it can be done automatically by placing the casing in an inserter being provided with a plunger which plunger is able to put pressure on the distal end of the casing. After insertion, the sharp needle 9 together with the needle hub 8 is retracted into the cavity of the casing and the casing is removed from the insertion site while the technical part is left in the obtained subcutaneous position while the sharp needle 9 is secured inside the cavity. According to several embodiments the spring unit 7 also after insertion exercises a force on the needle hub/sharp needle preventing the sharp needle from getting in contact with the surroundings, there by increasing the safety of the device.

Generally, in order for a technical part to remain in position after insertion, it is normally necessary to include attachment means attaching the technical part to the insertion site with larger force than the technical part is attached to the retracting sharp needle and needle hub.

Examples of such means are known to persons skilled within this technical field and the means can e.g. comprise 1) adhesive surfaces of the body part of the technical part which during insertion get in contact with corresponding surfaces of the insertion site, 2) mechanical means such as movable hooks getting caught between the body part of the technical part and the insertion site (see e.g. WO 2007/071255, FIG. 24), and/or 3) elastic means which during removal of the casing from the insertion site continuously pushes the technical part away from the casing thereby preventing that the attachment between the sharp needle and the technical part result in detachment of the technical part from the insertion site.

The attachment means releasably attaching the technical part—or subcutaneous unit—to corresponding means of the retracting sharp needle and needle hub are normally constituted by friction between a soft cannula of the technical part and the sharp needle. If the technical part does not comprise a soft cannula, the attachment means might comprise mechanical means which can be automatically moved as the technical part approached the injection site or which can be manually deactivated when the technical part as arrived at the final subcutaneous position.

Figure 3:
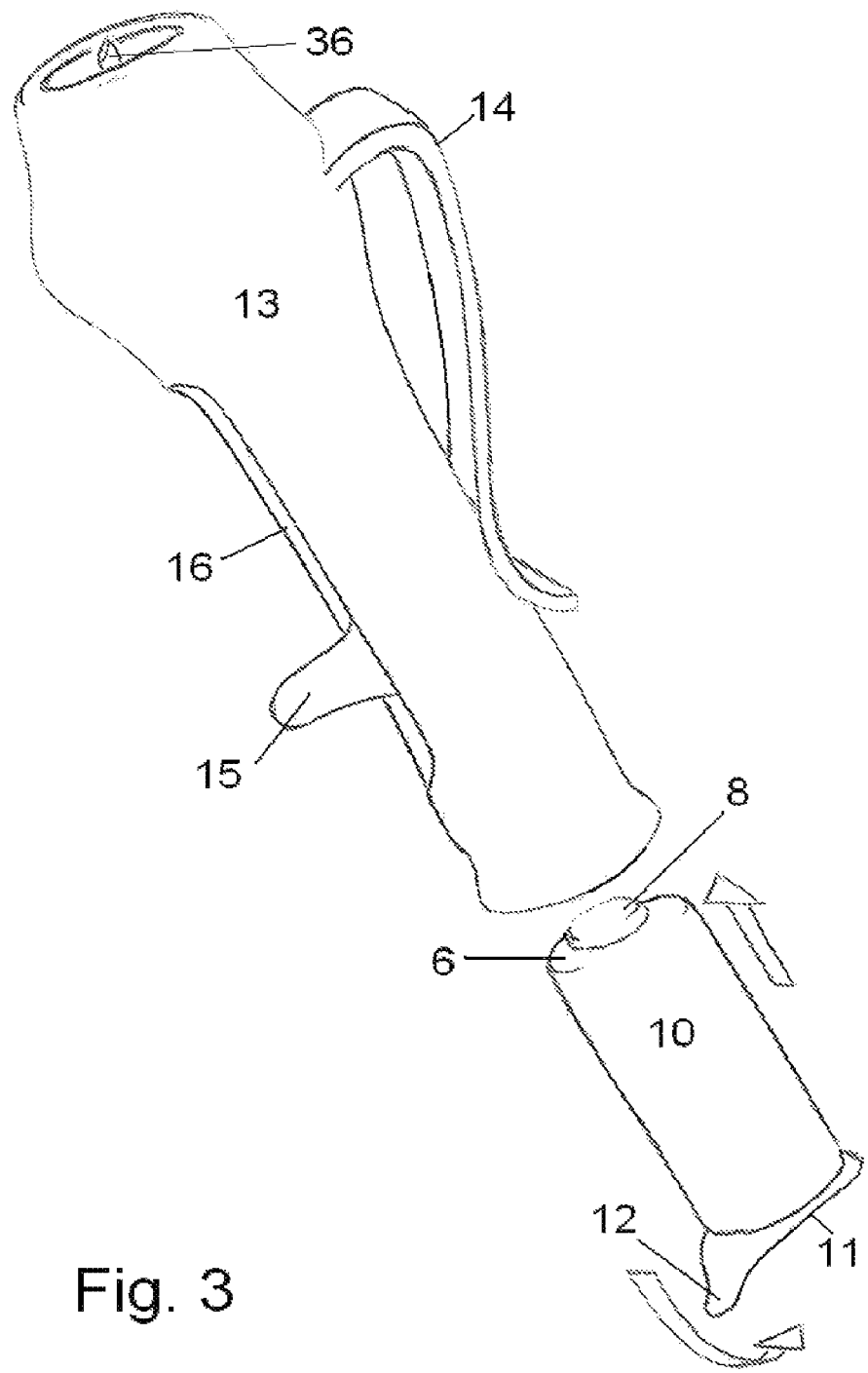
FIG. 3 shows an inserter for a single cavity embodiment of a holding device.

FIG. 3 shows an inserter for a single casing embodiment of a holding device according to the invention. The inserter comprises a housing 13 provided with a handle 14 by which the inserter can e.g. be attached to a pocket The reusable inserter has an open end where a holding device in the form of a disposable casing containing a technical part 1, 2 can be at least partly inserted and secured in such a way that the holding device cannot move relative to the inserter housing 13. This can be done e.g. by providing a thread on the inner surface of the inserter and provide a corresponding thread on the outer surface of the casing. Inside the housing of the inserter is a plunger positioned. The plunger can move from a retracted loaded resting position inside the inserter to a forward powered position where the plunger will get in physical contact with and actually penetrate the second side 6 of the casing and enter into the cavity of the holding device which is secured in the inserter. The plunger will move forward towards the open end of the inserter when it is activated.

Normally, an actuator 15 is used to activate the inserter. According to an embodiment, the actuator 15 protrudes through a longitudinal opening 16 in the housing 13. The actuator 15 is directly coupled to the not shown plunger and as the user pushes the actuator 15 towards the open end of the inserter, the plunger is pushed forward as well toward the second side 6 and the top of the needle hub 8 of the holding device. Upon contact with the casing, the plunger provide an impact on the flexible layer protecting the second side 6 and forces the technical part 1, 2 toward the patients skin. If the second side is constituted by a brittle, layer, the plunger penetrates the layer and forces the technical part 1, 2 toward the patient's skin.

Alternatively, the actuator 15 protruding through a longitudinal opening 16 in the housing 13 is coupled to a not shown spring, and as the user forces the actuator 15 backwards i.e. away from the open end, the not shown spring is loaded. When the actuator 15 is in the backward position, the user can by pushing a not shown release button, release the not shown spring which will then force the plunger forward. As the not shown spring pushes the plunger towards the open end of the inserter, the plunger will upon contact with the casing provide an impact on the flexible layer protecting the second side 6 and force the technical part 1, 2 toward the patient's skin. If the second side is constituted by a brittle layer, the plunger penetrates the layer and forces the technical part 1, 2 toward the patient's skin. The inserter can comprise a lancing device for providing blood testing. According to the shown embodiment a lancet 36 can extend through the open end of the inserter housing 13 opposite the opening which can receive the holding device. The lancet will shoot forward when actuated and immediately retract after having penetrated the skin into a chosen depth. Lancing of the skin will produce a drop of blood which can then be introduced to a separate meter e.g. determining the bloods momentary content of glucose. How the lancet is loaded and activated is not shown in the figure.

Figure 4:
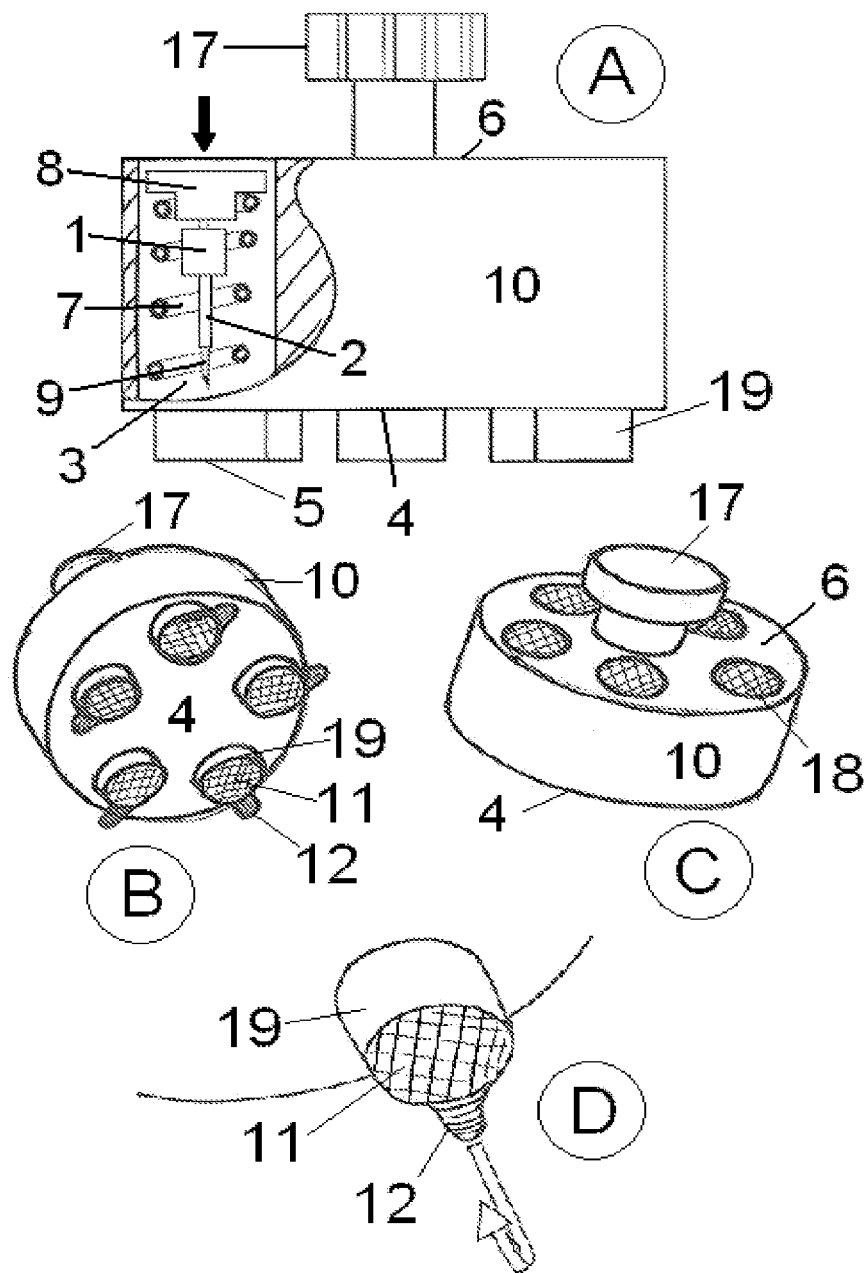
FIGS. 4A-D show a holding device having multiple cavities.

FIG. 4 shows a holding device according to the invention having multiple cavities 3 for technical parts 1, 2. The shown embodiment can hold five sterile technical parts ready to insert. The holding device comprises an attachment hub 17 which during use is either attached to an inserter or used as a handle by the user. Each of the five cavities is provided with a brittle, penetrable, layer 18 covering the second side of the casing cavity 3. This feature is shown in FIG. 4C. Also, each outlet opening 5 of the five cavities is covered with a sterility cover 11 and each sterility cover 11 is provided with a handle snip 12 which makes it possible for the user to remove the sterility cover before use. This feature is shown in FIGS. 4B and 4C.

FIG. 4A shows a partly cut-through view of the inside of the holding device. This view shows a technical part in the form of a cannula part provided with a body part 1 and a longish part 2 which is attached to a sharp needle 9. The sharp needle 9 extends from the needle hub 8 to which the sharp needle is secured. A spring unit 7 is positioned between a proximal surface of the needle hub 8 and a distal surface of the lower first side 4 of the casing. In the shown position, the spring unit 7 is un-biased and does not exercise any pressure on the needle hub 8 or the first side 4 of the casing. The casing also comprises guiding parts 19 which according to this embodiment is a protruding edge having a circular profile. The circular edge will correspond to a circular groove in the infusion site into which the technical part is to be inserted. The circular profile allows the user to rotate the holding device relative to the infusion site.

In a use situation, the sterility cover 11 is first removed from the chosen cavity 3 as shown in FIG. 4D, and then the outlet opening 5 is positioned correctly relative to an infusion site. When the outlet opening is positioned, the penetrable layer 18 covering the second side of the cavity 3 is subjected to an impact as indicated with an arrow in FIG. 4A. The impact can be provided using an inserter —either manual or automatic—or it can be provided using a manual tool such as a finger or a pencil. At the impact, the needle hub 8 is pushed down towards the first side 4 of the casing and the longish part 2 of the technical part is pushed out of the outlet opening 5 of the casing. The technical part is then, as a result of not shown attachment means which normally are part of the body part 1 of the technical part, attached to the infusion site and hereafter the spring unit 7 pushes the needle hub 8 and the sharp needle 9 back into the cavity 3 of the casing.

Figure 5:
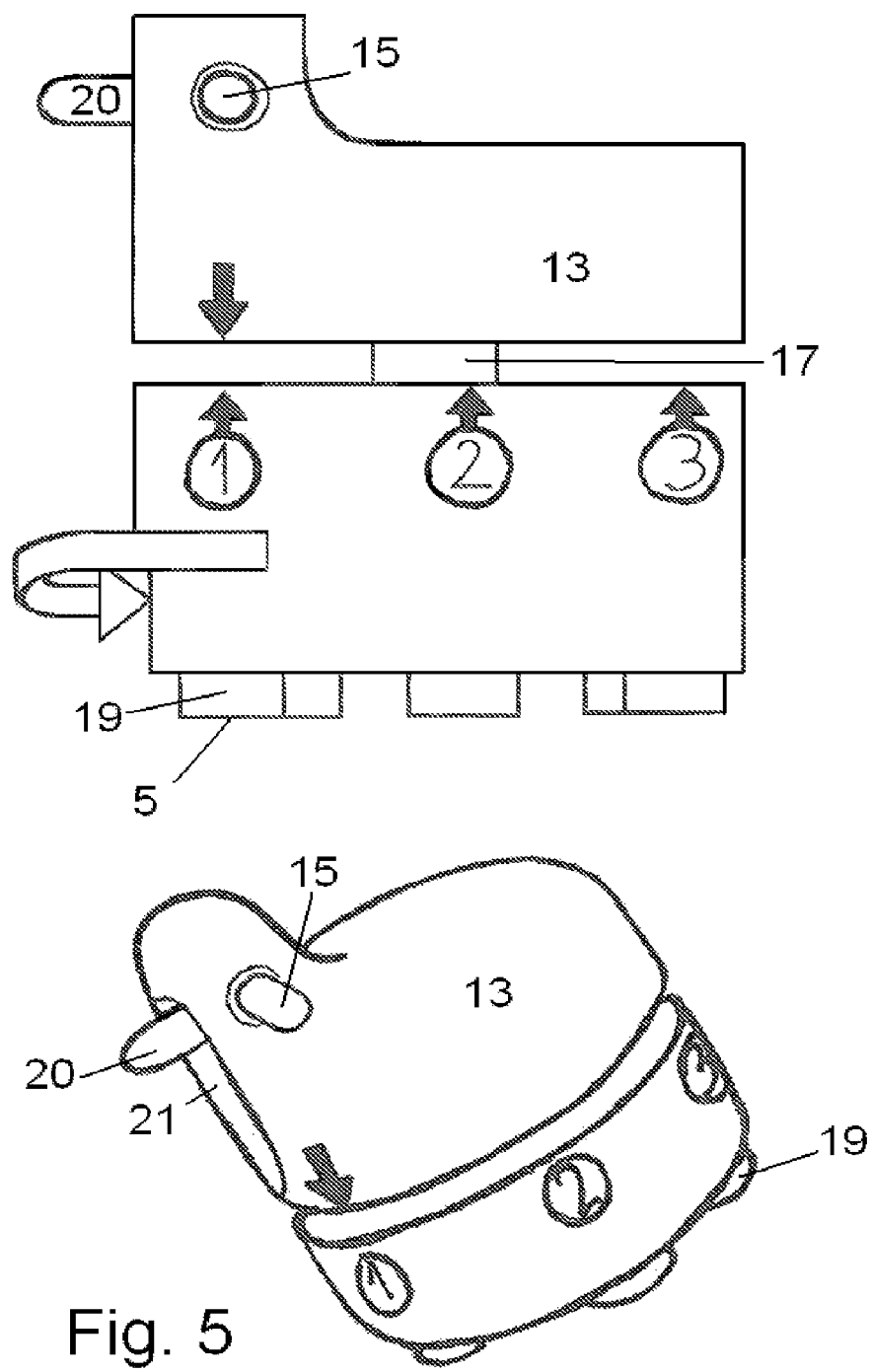
FIG. 5 shows an embodiment of an inserter having a multiple cavity holding device attached.

FIG. 5 shows the same holding device as FIG. 4 in combination with an inserter. The attachment hub 17 of the holding device is inserted and attached in a receiving section in the inserter. When the attachment hub 17 is attached to the inserter, it is possible to rotate the holding device relative to the inserter. The position of an indicator on the holding device (e.g. an arrow over an encircled number as shown in FIG. 5) and the position of an indicator on the inserter (e.g. a downward arrow) establish to the user when the holding device is positioned such that a given technical part is inserted. The inserter is provided with a double sided actuator 15 and when the user pushes the oppositely positioned buttons against each other, a plunger 22 is released and provides an impact to the second side 6 of the cavity 3 holding the indicated technical part in question. The inserter also comprises a reloading handle 20 which extends through a longitudinal opening 21 in the outer surface of the inserter. After the actuator 15 has been released and the plunger 22 forced into a forward position, the reloading handle 20 is pushed back to a distal position and this movement brings the plunger back to start position where after the plunger is ready to be released once again.

Figure 6:
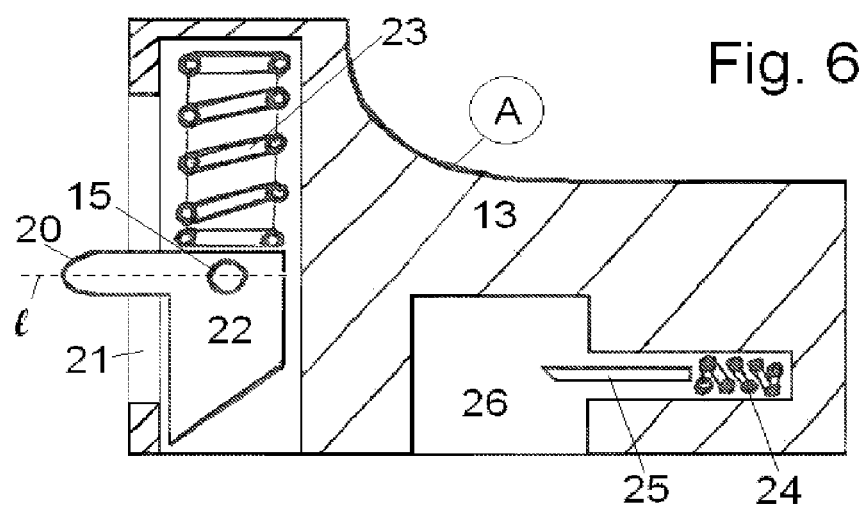
FIGS. 6A-C show cut-through views of the embodiment of the inserter shown in FIG. 5.
Figure 6:
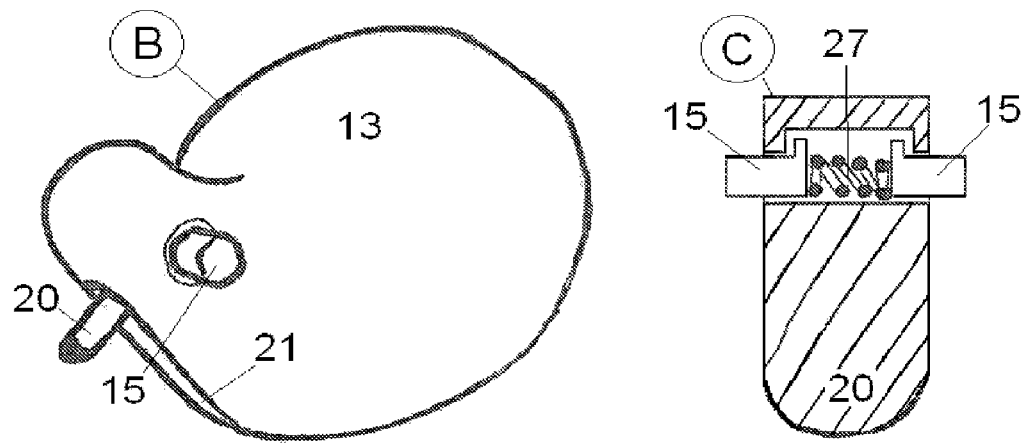

FIG. 6 shows a cut-through view of the same inserter as in FIG. 5. FIG. 6 shows how the plunger 22 is positioned in a narrow tube-shaped cavity the walls of which provide good guidance for the moving plunger 22. The plunger 22 can move between a forward and a retracted position in the tube-shaped cavity and the plunger 22 is forced to a forward position by the insertion spring 23. The reloading handle 20 extends through a longitudinal opening 21 in the tube-shaped path and the reloading handle extends to such a degree that it is possible for a user to manipulate the handle 20 from outside the inserter.

The inserter also comprises a receiving section 26 in the form of a cavity which is adapted to receive an attachment hub 17 of a holding device. In order to secure the attachment hub 17 in the receiving section 26, the receiving section 26 is provided with a locking part 25 which can slide between a forward and a retracted position. A locking spring 24 forces the locking part 25 into the forward position in which position the locking spring 24 is less based.

FIG. 6B shows the inserter from above and in this view both the actuator handles 15 and the reloading handle 20 can be seen. FIG. 6C shows a cut-through view of the plunger along the line l shown in FIG. 6A. The actuator handle 15 comprises two elastically mounted buttons. A release spring 27 is mounted between the two buttons 15 and the two buttons 15 extend through two oppositely positioned openings in the housing 13 of the inserter. When both buttons 15 are pushed towards each other simultaneously, the two buttons 15 will be pressed to a position inside the housing of the inserter and then the plunger 22 will be released from the retracted position and pushed forward by the insertion spring 23. When reloading the inserter, the user pushes the reloading handle 20 upwards/backwards. When the buttons reach a position in line with the oppositely positioned openings in the housing 13, the buttons 15 will be pushed out of the openings by the release spring 27 and the plunger 22 will again be locked in the retracted position.

Figure 7A:
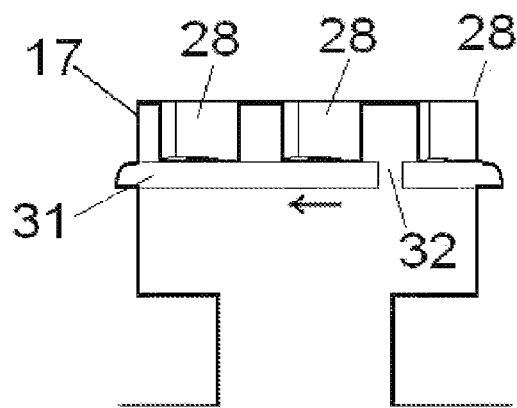
FIGS. 7A-B show details of the on the attachment means on the multiple cavity holding device.
Figure 7B:
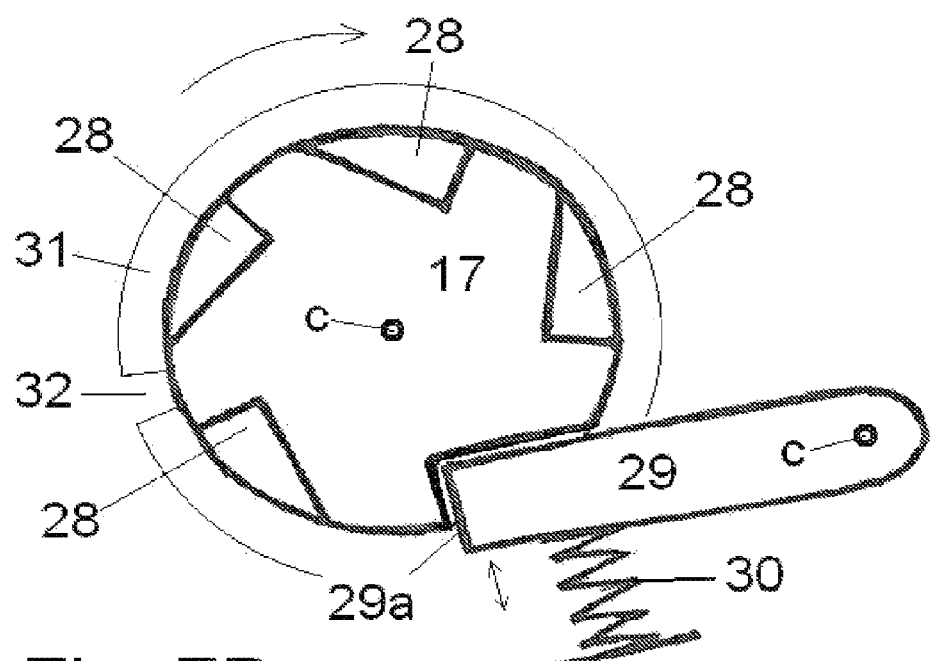

FIG. 7A shows a side view of an embodiment of an attachment hub 17 of a holding device. FIG. 7B shows a top view of the attachment hub of FIG. 7A including a pivotal part and a spring integrated with the inserter.

The attachment hub 17 of FIGS. 7A and 7B comprises a top level of inclined openings 28 which openings 28 prevent the holding device being turned in the wrong direction, i.e. turned to the left according to the shown embodiment, when the user wants to position the next technical part in front of the plunger 22 of the inserter. The inserter is inside the receiving section corresponding to receiving section 26 of FIG. 6, provided with a mechanism assuring that the inserter—when turned right will—perform a stepwise rotating movement. The mechanism comprises a pivotal part 29 which is attached to a lateral spring 30. The lateral spring 30 pushes the pivotal part 29 toward the centre of the receiving section 26 and toward the central part of the attachment hub 17 when the attachment hub 17 is inserted into the receiving section 26. When the attachment hub 17 is turned to the right, the pivotal part 29 can slide along the long wall of the opening 28 and the outer surface of the attachment hub 17 until a new opening 28 is reached. The lateral spring 30 will thereby push the pivotal part 29 into the opening 28. If it is attempted to turn the attachment hub 17 to the left, i.e. counter to the shown arrow, the contact between the short wall of the opening 28 and the flat front surface 29*a* of the pivotal part 29 will prevent this movement.

The attachment hub 17 also comprises a second level constituted with a round going protruding edge 31. As the locking spring 24 pushes the locking part 25 (shown in FIG. 6) towards the centre of the receiving section and towards the body of the attachment hub 17, it will be possible, to push the attachment hub 17 into the receiving section 26 with the top first at any angular position as the locking part 25 is elastically mounted and as the protruding edge 31 and/or the locking part 25 is provided with an inclining surface in+the direction pointing towards the contact surface during insertion. The locking part 25 will therefore be pushed backwards against the force of the locking spring 24 when the attachment hub 17 is pushed into the receiving section and as the surface opposite the contact surface of the protruding edge 31 and/or the locking member 25 is flat, the locking part 25 will be secured behind the protruding edge 31 after the attachment hub 17 has been fully inserted into the receiving section 26. At one position an upward opening 32 is provided in the protruding edge 31 which allows for the locking part 25 to pass through the protruding edge 31 and for the attachment hub 17 to be removed from the receiving section 26 and the inserter.

The rotational centre c of respectively the attachment hub 17 and the pivotal part 29 is marked with a "c".

Generally, there are many ways for a skilled person to add mechanisms to secure the attachment of the holding device to the inserter and to further control the stepwise turning of the inserter relative to the holding device in order to control the insertion of each new technical part.

When a user wants to employ a holding device according to the shown embodiment with the illustrated inserter, the user first will first have to secure the holding device to the inserter. As the inserter does not comprise a sharp needle and does not get in contact with the patient's blood at any time, the inserter needs not be kept in a sterile packing. Also, the holding device might be kept in an ordinary non-sterile packing as the sterility of each of the technical parts are maintained locally inside each cavity of the casing.

After having secured the holding device to the inserter by pushing the attachment hub 17 into the receiving section 26 of the inserter, the user makes sure that the inserter indicator and the indicator of the holding device, points to insertion of the desired technical part. Then the user removes the sterility cover 11 covering the first side of the casing e.g. by pulling a snip 12, and next places the guiding parts 19 of the open end of the first side of the casing against a corresponding surface of an infusion site. When the holding device is correctly positioned, the user activates the actuator 15 of the inserter and the plunger 22 of the inserter is released and moves forward into the cavity holding the chosen technical part. The plunger 22 makes contact with the needle hub 8 and forces the technical part out through the outlet 5 of the first side of the holding device and into a secured position in the infusion site. When the technical part is in the secured position, the needle hub 8 is pushed backward by the return spring 7 while the technical part remains in the secured position in the infusion site. The inserter can then be reloaded while the holding device is still in the insertion position in order to assure that all downward pressure has been removed from the needle hub 8.

After reloading the inserter, the position of the holding part relative to the inserter can be re-adjusted in order to position a new technical part for insertion e.g. by turning the holding device one step right relative to the inserter, and then the combined device is again ready for inserting a technical part.

When there are no more sterile technical parts in the holding device or when the user wants to apply a different holding device with the inserter e.g. a holding device comprising sensors instead of e.g. cannula parts as technical parts, the holding device is positioned relative to the inserter in such a way that the locking part 25 can pass through the opening 32 and the holding device then can be released from the inserter.

Figure 8:
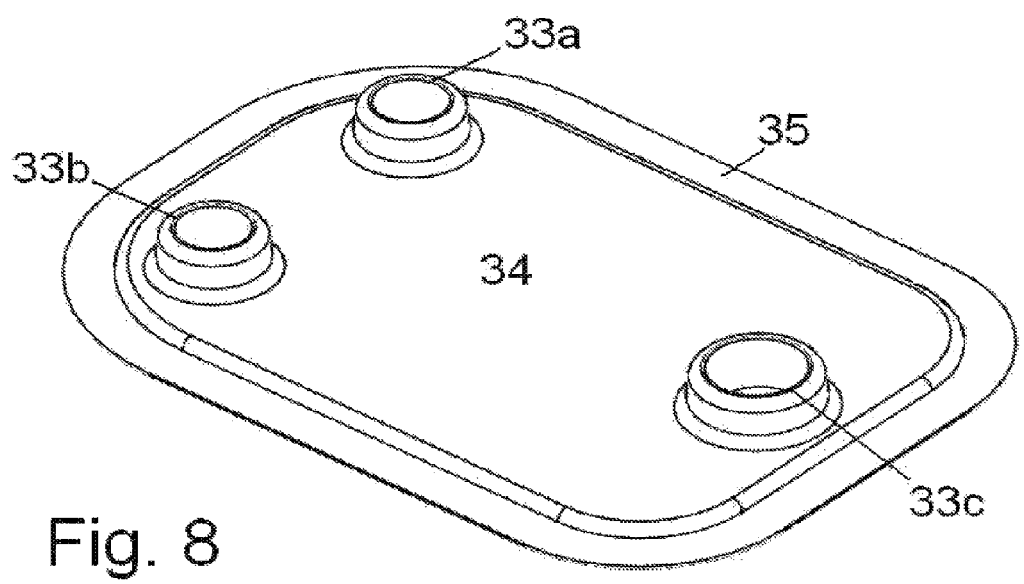
FIG. 8 shows a patch base to be used with a holding device according to the invention.

FIG. 8 shows an infusion site with which a holding device according to the invention can be applied. The shown infusion site is a patch base comprising a relatively rigid plate 34 provided with three receiving positions provided with guiding parts 33 to easily position the corresponding guiding parts 19 of the holding device. The rigid plate 34 is provided with a mounting pad 35 in order to make it possible to attach the plate 34 to a patient's skin. In the shown embodiment it would be possible to e.g. position a technical part in form of a cannula part at the receiving positions provided with guiding parts 33a first and e.g. position a technical part in form of a sensor part in the receiving positions provided with guiding parts 33c. After 3 days a new technical part in form of a cannula part could be positioned at the receiving positions provided with guiding means 33b and the first cannula part could e.g. be removed. After yet three days the whole plate 34 including the working cannula part and the working sensor part could be removed and a new patch base could be placed at another position of the patient's body.

Generally, the infusion site can have many forms. The infusion site can e.g. be 1) a patch base having a single cannula port i.e. a receiving section for a cannula part, 2) a patch base having 1-2 cannula ports and a sensor port, i.e. a receiving section for a sensor part, 3) a traditional infusion site comprising one cannula port, 4) an injection port, i.e. a small unit allowing for multiple injections with syringe or injection pen, 5) a sensor device provided with one sensor port, 6) a combination device provided with one cannula port and one sensor port, 7) a combination device provided with two cannula ports and 1 sensor port, or 8) a patch base having more than two cannula ports and/or more than one sensor port.

FIG. 9 shows a single inserter combined with two holding devices. The first holding device has five outlets and therefore holds five technical parts in the form of sensor parts. The second holding device has 10 outlets and therefore holds 10 technical parts in the form of cannula parts.

The oppositely pointing arrows on respectively the inserter housing 13 and each holding device are indicators showing which technical part is to be inserted.

The actuator 15 of the inserter has a resting position at the middle of the longitudinal opening 16. When a technical part is to be inserted from the first holding device, the indicator of the first holding device is first brought to a position where a new technical part is placed and then the actuator 15 is pressed towards the first holding device. When a technical part is to be inserted from the second holding device, the indicator of the second holding device is brought into a position where a new technical part of the second holding device is placed and then the actuator 15 is pressed towards the second holding device.

The inserter can be reloaded by bringing the actuator 15 back to the indicated middle position.

FIGS. 9B and 9C show a view of each holding device from the first side. The holding device of FIG. 9B corresponds to the holding placed upwards in FIG. 9A where this holding device is holding five sensor parts. The holding device of FIG. 9C corresponds to the holding device placed downwards in FIG. 9A where this holding device is holding ten cannula parts. As each cannula part can normally work for three days, and a sensor part can normally work for 6 days, the two holding devices combined with the inserter of FIG. 9A could provide a user with adequate technical parts for a period of 30 days.

The inserter comprises a lancing device for providing blood testing although the lancing device is hidden behind a cover. The lancet will shoot forward when actuated by pressing the actuator 37 toward the cover and immediately retract after having penetrated the skin into a chosen depth. Lancing of the skin will produce a drop of blood which can then be introduced to a separate meter e.g. determining the bloods momentary content of glucose.

| Ref. No. | Name of unit |
|---|---|
| 1 | Body part of technical part |
| 2 | Longish part of technical part |
| 3 | Cavity of casing |
| 4 | First side of casing |
| 5 | Outlet of casing |
| 6 | Second side of casing |
| 7 | Return spring e.g. flexible layer of casing |
| 8 | Needle hub |
| 9 | Sharp needle/insertion needle |
| 10 | Sides of casing extending in direction of insertion |
| 11 | Sterility cover covering first side of casing |
| 12 | Snip of cover |
| 13 | Housing of inserter |
| 14 | Handle of inserter |
| 15 | Actuator of inserter |
| 16 | Longitudinal opening for actuator |
| 17 | Attachment hub |
| 18 | Penetratable layer of casing |
| 19 | Guiding parts |
| 20 | Reloading handle |
| 21 | Longitudinal opening for reloading handle |
| 22 | Plunger |
| 23 | Insertion spring |
| 24 | Locking spring |
| 25 | Locking part |
| 26 | Receiving section for attachment hub |
| 27 | Release spring |
| 28 | Inclined openings in attachment hub |
| 29 | Pivotal part |
| 29a | Flat front surface of pivotal part |
| 30 | Lateral spring |
| 31 | Protruding edge |
| 32 | Upward opening in protruding edge |
| 33, 33a, 33b, 33c | Guiding parts of infusion site |
| 34 | Rigid plate |
| 35 | Mounting pad |
| 36 | Lancet |
| 37 | Actuator for lancet |

The invention claimed is:

1. A holding device holding subcutaneous units under sterile conditions, the holding device comprising: a casing providing at least two closed cavities each comprising walls where the walls encompass a subcutaneous unit, each cavity having a first side comprising an outlet opening, the outlet opening before use is covered with a penetrable or removable cover, and a second side comprising a layer having an outer surface and being penetrable in order to transfer an impact from outside the layer to the held subcutaneous unit, the casing comprising a needle upon which the subcutaneous unit is releasably attached and a spring unit providing retraction of the needle after insertion of the subcutaneous unit, the needle extending from a needle hub retained in each cavity; wherein an impact towards the outer surface of the layer of the second side pushes the subcutaneous unit and the needle at least partly out of the casing and into a subcutaneous position, when the subcutaneous unit is released from the needle allowing detachment of the subcutaneous unit from the casing.

2. The holding device according to claim 1, wherein the holding device comprises an attachment hub attaching the holding device to and interacting with an inserter able to provide an impact toward the outer surface of the layer of the second side of the casing.

3. The holding device according to claim 1, wherein the spring unit comprises an elastic unit positioned between the distal end of the needle or of a proximal surface of a needle hub to which the needle is attached and the first side such that the elastic unit pushes the needle into a retracted position after detachment of the subcutaneous unit.

4. The holding device according to claim 1, wherein the subcutaneous unit is configured to be attached to an infusion site at a point during insertion of the subcutaneous unit where the subcutaneous unit has reached a final subcutaneous position, wherein the infusion site before insertion comprises at least a part of or the complete first side of the holding device and the infusion site is provided with a mounting pad to permanently attach the infusion site to the patient's skin surface.

5. The holding device according to claim 4, wherein a proximal side of the subcutaneous unit is configured to be attached to the infusion site at a point during insertion of the subcutaneous unit where the subcutaneous unit has reached a final subcutaneous position.

6. The holding device according to claim 4, wherein the casing comprises guiding parts corresponding to receiving or guiding parts of the infusion site, where joining of the corresponding guiding parts ensures correct positioning of the casing before insertion relative to the infusion site.

7. The holding device according to claim 1, wherein the subcutaneous unit comprises a body part, the body part after detachment from the holding device is positioned above the patient's skin surface and a longish part which after detachment from the holding device is positioned below the patient's skin surface in a depth below the skin surface between about 1-15 mm.

* * * * *